US 007525001B2

(12) United States Patent
Kim et al.

(10) Patent No.: US 7,525,001 B2
(45) Date of Patent: Apr. 28, 2009

(54) PROCESS FOR PREPARATION OF 2,6-DIALKYLTETRALIN

(75) Inventors: Young Gyu Kim, Gunpo-si (KR); Woon Ki Kim, Seongnam-si (KR); Byung Hyun Kim, Jeollanam-do (KR); Jong Gil Lee, Incheon (KR)

(73) Assignee: Seoul National University Industry Foundation, Seoul (KR)

( * ) Notice: Subject to any disclaimer, the term of this patent is extended or adjusted under 35 U.S.C. 154(b) by 779 days.

(21) Appl. No.: 11/065,035

(22) Filed: Feb. 25, 2005

(65) Prior Publication Data
US 2006/0020153 A1 Jan. 26, 2006

(30) Foreign Application Priority Data
Jul. 21, 2004 (KR) .............. 10-2004-0056835

(51) Int. Cl.
C07C 2/68 (2006.01)
C07C 1/20 (2006.01)
(52) U.S. Cl. .............. 585/323; 585/467; 585/469; 585/410; 585/411
(58) Field of Classification Search .......... 585/323, 585/467, 469, 410, 411
See application file for complete search history.

(56) References Cited

U.S. PATENT DOCUMENTS

| 3,936,509 | A | 2/1976 | Nagahama et al. |
| 3,957,896 | A | 5/1976 | Yokoyama et al. |
| 3,966,624 | A | 6/1976 | Duling et al. |
| 3,987,078 | A | 10/1976 | Dickason |
| 3,996,031 | A | 12/1976 | Chong |
| 4,013,705 | A | 3/1977 | Bushick |
| 4,014,949 | A | 3/1977 | Hedge |
| 4,034,052 | A | 7/1977 | Puskas |
| 4,041,089 | A | 8/1977 | Allen et al. |
| 4,064,072 | A | 12/1977 | Bushick |
| 4,073,819 | A | 2/1978 | Seitzer |
| 4,556,751 | A | 12/1985 | Maki et al. |
| 4,740,647 | A | 4/1988 | Hussmann et al. |
| 4,777,312 | A | 10/1988 | Bakas et al. |
| 4,783,569 | A | 11/1988 | Hussmann et al. |
| 4,783,570 | A | 11/1988 | Hussmann et al. |
| 4,791,235 | A | 12/1988 | Maki et al. |
| 4,940,832 | A | 7/1990 | Miyashi et al. |
| 4,950,825 | A | 8/1990 | Sikkenga et al. |
| 4,962,260 | A | 10/1990 | Sikkenga et al. |
| 4,982,040 | A | 1/1991 | Angevine et al. |
| 4,992,619 | A | 2/1991 | Koide et al. |
| 5,001,295 | A | 3/1991 | Angevine et al. |
| 5,004,853 | A | 4/1991 | Barger et al. |
| 5,012,024 | A | 4/1991 | Sikkenga et al. |
| 5,030,568 | A | 7/1991 | Carlson et al. |
| 5,055,612 | A | 10/1991 | Tachibana et al. |
| 5,059,742 | A | 10/1991 | Miyashi et al. |
| 5,073,670 | A | 12/1991 | Sikkenga et al. |
| 5,118,892 | A | 6/1992 | Sikkenga et al. |
| 5,132,224 | A | 7/1992 | Mueller et al. |
| 5,138,098 | A | 8/1992 | Hagen et al. |
| 5,189,234 | A | 2/1993 | Amelse |
| 5,198,594 | A | 3/1993 | Lillwitz et al. |
| 5,220,098 | A | 6/1993 | Nakamura et al. |
| 5,242,825 | A | 9/1993 | Mueller et al. |
| 5,254,769 | A | 10/1993 | Takagawa et al. |
| 5,268,523 | A | 12/1993 | Fellmann et al. |
| 5,276,230 | A | 1/1994 | Inamasa et al. |
| 5,292,934 | A | 3/1994 | Sikkenga et al. |
| 5,321,178 | A | 6/1994 | Inamasa et al. |
| 5,334,796 | A | 8/1994 | Lillwitz et al. |
| 5,396,007 | A | 3/1995 | Kyuko et al. |
| 5,396,008 | A | 3/1995 | Ozawa et al. |
| 5,401,705 | A | 3/1995 | Amelse |
| 5,401,892 | A | 3/1995 | Sikkenga et al. |
| 5,442,103 | A | 8/1995 | Iwane et al. |
| 5,446,226 | A | 8/1995 | Ozawa et al. |
| 5,481,055 | A | 1/1996 | Takagawa et al. |
| 5,495,060 | A | 2/1996 | Takagawa et al. |
| 5,510,563 | A | 4/1996 | Smith et al. |
| 5,670,704 | A | 9/1997 | Hagen et al. |
| 5,744,670 | A | 4/1998 | Motoyuki et al. |
| 5,840,970 | A | 11/1998 | Sumner, Jr. et al. |
| 5,844,064 | A | 12/1998 | Motoyuki et al. |
| 5,948,949 | A | 9/1999 | Takagawa et al. |
| 5,955,641 | A | 9/1999 | Chen et al. |
| 5,977,426 | A | 11/1999 | Smith et al. |

(Continued)

OTHER PUBLICATIONS

Robert Millini et al., "A Priori Selection of Shape-Selective Zeolite Catalysts for the Synthesis of 2,6-Dimethylnaphthalene", Journal of Catalysis 217 (2003) 298-309.
Yoshio Iwai et al., "Adsorption of Supercritical Carbon Dioxide + 2,6 and 2,7-Dimethylnaphthalene Isomers on NaY-Type Zeolite", Ind. Eng. Chem. Res. 2003, 42, 5261-5267.
P. W. Storms et al., "Bifunctional Derivatives of 2,6-Dimethyylnaphthalene", Journal of Chemical and Engineerint Data, Marathon Oil Company, Denver Research Center, Littleton, Colo., vol. 11, No. 2, Apr. 1966.
Dae Hyun Choo, "Cycloisomerization of 5-(O-tolyl)-Pentene Over Modified Zeolite BEA", Journal of Catalysis 207, 183-193 (2002).
Yoshio Iwai, "Separation of Isomeric Dimethylnaphthalene Mixture in Supercritical Carbon Dioxide by Using Zeolite", Ind. Eng. Chem. Res., 1994, 33, 2157-2160.

(Continued)

Primary Examiner—Thuan Dinh Dang
(74) Attorney, Agent, or Firm—Hunton & Williams LLP

(57) ABSTRACT

The present invention provides a novel process for highly selective preparation of 2,6-dialkyltetralin, a key precursor for 2,6-dimethylnaphthalene (2,6-DMN), which does not require an extra step for purifying various isomers obtained from the conventional processes for 2,6-DMN. The present invention is advantageous to improve the synthetic yield, to simplify the operation and thus to reduce the production cost, since different starting materials and different pathways are exploited and thus the additional steps are not necessary.

19 Claims, 1 Drawing Sheet

U.S. PATENT DOCUMENTS

| | | | |
|---|---|---|---|
| 6,011,190 | A | 1/2000 | Motoyuki et al. |
| 6,015,930 | A | 1/2000 | Santilli et al. |
| 6,018,086 | A | 1/2000 | Motoyuki et al. |
| 6,018,087 | A | 1/2000 | Motoyuki et al. |
| 6,057,487 | A | 5/2000 | Munson et al. |
| 6,072,098 | A | 6/2000 | Takagawa et al. |
| 6,121,501 | A | 9/2000 | Motoyuki et al. |
| 6,147,270 | A | 11/2000 | Pazzucconi et al. |
| 6,232,517 | B1 | 5/2001 | Pazzucconi et al. |
| 6,284,920 | B1 | 9/2001 | Paschke et al. |
| 6,461,700 | B2 | 10/2002 | Paschke et al. |
| 6,472,576 | B1 | 10/2002 | Bergstrom et al. |
| 6,495,710 | B2 | 12/2002 | Macek et al. |
| 6,504,069 | B1 | 1/2003 | Kyuuko et al. |
| 6,525,235 | B2 | 2/2003 | Yoshida et al. |
| 6,706,939 | B2 | 3/2004 | Nakao et al. |
| 6,717,009 | B2 | 4/2004 | Motoyuki et al. |
| 6,747,171 | B2 | 6/2004 | Rosen |
| 6,756,509 | B2 | 6/2004 | Nagase et al. |

OTHER PUBLICATIONS

Shu-Bin Pu, Synthesis of 2,6-Dimethylnaphthalene by Methylation of Methylnaphthalene on Various Medium and Large-Pore Zeolite Catalysts, Applied Catalysis A: General 146 (1996) 305-316.

Young Dae Kim, "The Application of Simulated Moving Bed Chromatography for the Separation Between 2,6 and 2,7-Dimethylnaphthalene", Korean J. Chem. Eng. 18(6), 971-976 (2001).

T. Chen et al., "Three-Step Reactions for Selective Production of 2,6-Rich Dimethylnaphthalene From 2,7-Rich Dimethylnaphthalene", Cataysis Today 93-95 (2004) 371-376.

L.D. Lillwitz, "Production of Dimethyl-2,6-Naphthalenedicarboxylate: Precursor to Polyethylene Naphthalate", Applied Catalysis A: General 221 (2001) 337-358.

PROCESS FOR PREPARATION OF 2,6-DIALKYLTETRALIN

CROSS REFERENCE TO RELATED APPLICATIONS

We claim priority from Republic of Korea Application No. 10-2004-0056835 filed Jul. 21, 2004, the entire contents of which are incorporated herein by reference.

TECHNICAL FIELD

The present invention relates to a novel processes for selective preparation of 2,6-dialkyltetralin. More particularly, the present invention is directed to a process for preparation of 2,6-dimethyltetralin (2,6-DMT) comprising the reaction steps: i) alkylating aromatic compound with alkene compounds to produce the first intermediates; ii) reducing the first intermediates to produce the second intermediates; and iii) cyclizing the second intermediates to produce 2,6-dimethyltetralin.

BACKGROUND 2,6-Dimethyltetralin (hereinafter, referred to as "DMT") is one of dialkyltetralins, herein the alkyl group is methyl, and a precursor of 2,6-dimethylnaphthalene (hereinafter, referred to as "DMN"). 2,6-DMN is a starting material to prepare 2,6-dimethylnaphthalate.

Industrially, 2,6-DMT is converted to 2,6-DMN by dehydrogenation in the presence of catalyst. The dehydrogenation process using the catalytic system, have been disclosed in U.S. Pat. No. 5,118,892, U.S. Pat. No. 5,189,234, U.S. Pat. No. 3,775,498 and U.S. Pat. No. 3,781,375. This reaction can be accomplished under gaseous or aqueous conditions. Preferably 2,6-DMT can be dehydrogenated in a gas state in the presence of catalyst at 600 ~900° F. under 0.01~25 bar at 0.1~20/h of weight hourly space velocity.

Dimethyl 2,6-naphthalenedicarboxylate, that can be derived from 2,6-DMN, is a raw material of liquid crystal polymers, polyethylenenaphthalate (PEN) that is the precursor for highly functional polyester resins, and the like. Presently, several chemical companies retain its synthetic technique and a small number of company in the world has commercialized it.

Recently, PEN has attracted much attention as an engineering plastic of high performance for the next generation, since it has much better physical properties than those of PET that are used currently worldwide. In practice, the new products obtained from the PEN resins have the better crystal properties and the higher softening points than those from the commercially available PET resins. Besides, the PEN resins show much better performance in mechanical strength, thermal stability, resistance to chemicals, gas permeability, atmosphere corrosion resistibility, electrical insulation and the like.

Therefore, the demand for PEN will be enormous if a cost-effective process for the preparation of its starting material, 2,6-naphthalenedicarboxylic acid (hereinafter, referred to as "NDCA"), is developed and commercialized in a large scale. Concretely, PEN has potential applications for fast spinning fiber, 8 mm tapes and plastic bottles as a raw material, and for videotapes and special functional films as an end product.

The methods for preparing 2,6-NDCA have been already disclosed to those skilled in this art. Precisely, U.S. Pat. No. 3,856,855 has illustrated the process for preparation of NDCA comprising a step oxidizing DMN with molecular oxygen by using a co-catalyst system such as Co/Mn/Br in the presence of 4% wt or more of acetic acid per DMN % wt under 2~8 bar of oxygen partial pressure at 100~160° C. That is to say, 2,6-DMN is a major source material to manufacture 2,6-NDCA industrially at present.

In addition, Sikkenga et al. have demonstrated methods for preparation of 2,6-DMN in U.S. Pat. No. 5,073,670; U.S. Pat. No. 5,401,892; U.S. Pat. No. 5,118,892; U.S. Pat. No. 5,012,024; and U.S. Pat. No. 5,030,781 and so on. Concretely, the synthetic process composed of the multi-step reaction in liquid phase has been disclosed in those literatures. In that methods specific alkenyl benezene is cyclized to one or more specific DMTs in the presence of a proper catalyst of acidic solid, such as acidic crystal zeolite; are dehydrogenated to produce the corresponding DMNs; and then, the resulting DMNs are isomerized to obtain the specific DMN.

On the other hand, Thompson has illustrated the method for isomerization in U.S. Pat. No. 3,775,496, in which 5-(m-tolyl)-pent-2-ene is cyclized to 1,6-DMT and 1,8-DMT and then they are dehydrogenated to 1,6-DMN and 1,8-DMN and again the obtained DMNs are isomerized to 2,6-DMN and 2,7-DMN respectively. In addition, Thompson has disclosed in U.S. Pat. No. 3,775,498 that 5-(m-tolyl)-pent-2-ene is cyclized to 1,5-DMT; is dehydrogenated to 1,5-DMN; and then isomerized to 2,6-DMN.

Furthermore, Amoco (US) company has developed a process for preparation of 2,6-DMN comprising steps (1) adopting ortho-xylene as a starting material, alkenylation with 1,3-butadiene to prepare alkenyl benzenes; (2) cyclizing to obtain 1,5-DMT; then (4) dehydrogenation to prepare 1,5-DMN; and again (5) isomerization to 2,6-DMN and succeeded in business. Unfortunately, this process is complicated and problematic because a number of by-products such as 1,6-DMN are generated in the isomerization step to decrease the yield of the overall process (D. L. Sikkenga; I. C. Zaenger; G. S. Williams, U.S. Pat. No. 5,030,781 (1991): D. L. Sikkenga; I. C. Zaenger; G. S. Williams, U.S. Pat. No. 5,118,892 (1992): L. D. Lillwitz; A. M. Dkarachewski, U.S. Pat. No. 5,198,594 (1993)).

Also, Teijin (Japan) company has manufactured 2,6-DMN by alkylation or acylation of naphthalene or methylnaphthalene as a starting material. However, this process is not appropriate for production of 2,6-DMN in a large scale, due to the reaction efficiency, the lifetime of catalyst, the actual reaction conditions and the like (K. Sumitani; K. Shimada, Japanese Patent Application No. 1992-013637: K. Sumitani; K. Shimada, Japanese Patent Application No. 1992-112839: T. Fujita; K. Sumitani; K. Shimada, Japanese Patent Application No. 1992-049252).

In summary, the above-mentioned methods for preparation of 2,6-DMN, have mostly adopted 1-(o-, m-, or p-tolyl)pent-1 or -2-ene type of straight chained alkene compounds as the starting materials, and thus require the acidic catalysts for the cyclization.

Accordingly, after the dehydrogenation step, the reaction mixture contains different isomers of DMN, contaminants, by-products, remained DMT and alkenyl benezene as well as 2,6-DMN. Therefore, some extra steps of isomerization and separation are needed to obtain pure 2,6-DMN.

In order to obviate above-mentioned problems fundamentally, the present inventors have tried to exploit different starting materials and exclude the isomerization steps through different pathways of alkylation and cyclization in the process for preparation of 2,6-DMN, and consequently, have developed a novel process for highly selective preparation of 2,6-dialkyltetralin in a high yield.

BRIEF DESCRIPTION OF THE DRAWINGS

The objects, features and other advantages of the present invention will be more clearly understood from the following detailed description taken in conjunction with the accompanying drawings, in which.

DISCLOSURE OF THE INVENTION

Figure 1:
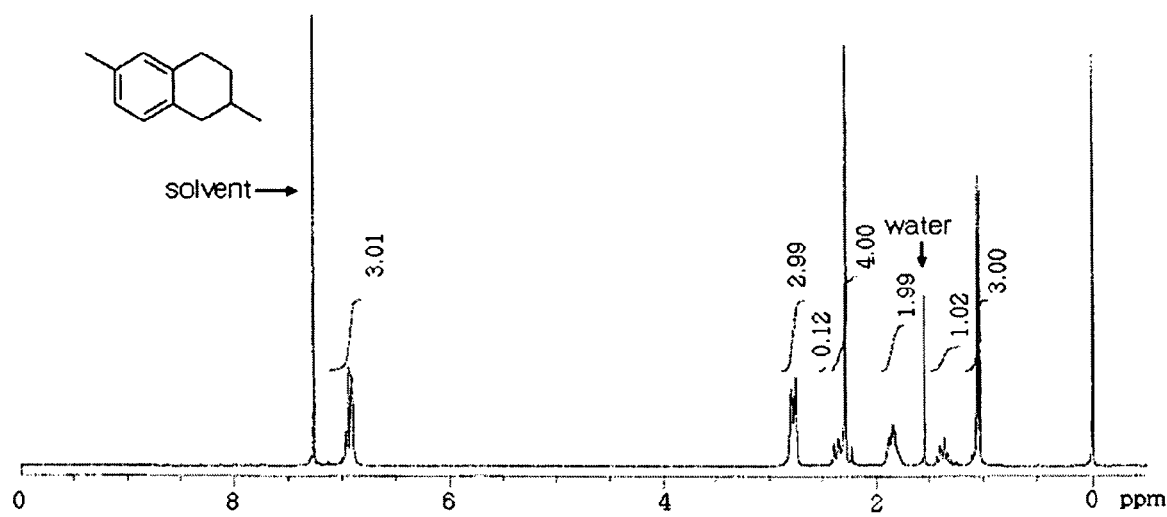
FIG. 1 illustrates the $^1$H NMR (300 MHz) spectrum of 2,6-dimethyltetralin (in CDCl$_3$) of the present invention, prepared in Example 1.

The primary object of the present invention is to provide a process for the preparation of 2,6-dialkyltetralin by cyclization of a compound of formula (9) prepared through a process which comprises: i) a step for alkylating aromatic compound of formula (1) with alkene compound of formula (2) in the presence of catalyst to produce the reaction products of formula (3) to formula (8); and ii) a step for reducing the reaction products obtained in the above step i) to produce formula (10).

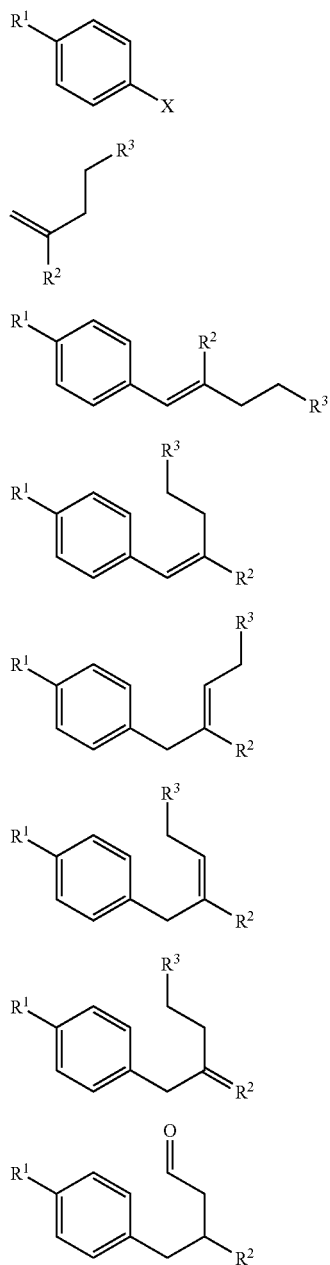

Another object of the present invention is to provide a novel process for the preparation of a compound of formula (9) which comprises: i) a step for alkylating aromatic compound of formula (1) with alkene compound of formula (2) in the presence of catalyst to produce the reaction products of formula (3) to formula (8); and ii) a step for reducing the reaction products obtained in the above step i) to produce a compound of formula (9).

Further object of the present invention is to provide a process for the preparation of a mixture of 2,6-dialkyltetralin and 2,6-dilkylnaphthalene through concurrent cyclization and dehydrogenaion of a compound of formula (9) in the presence of Lewis acid catalyst or ion exchange resin catalyst.

Still another object of the present invention is to provide a use of the compound of formula (9) as an intermediate for the preparation of 2,6-dialkyltetraline and/or 2,6-dialkylnaphtalene.

Additional advantages, objects and features of the present invention will be set forth in part in the description which follows and in part will become apparent to those ordinarily skilled in the art upon examination of the followings or may be learned from Examples of the present invention.

In order to attain the above-mentioned object of the present invention, the present invention provides a process for the preparation of a compound of formula (9) which comprises: i) a step for alkylating aromatic compound of formula (1) with alkene compound of formula (2) in the presence of catalyst to produce the reaction products which comprises q compounds of formula (3) to (8); and ii) a step for reducing the reaction products obtained in the above step i) to produce a compound of formula (9),

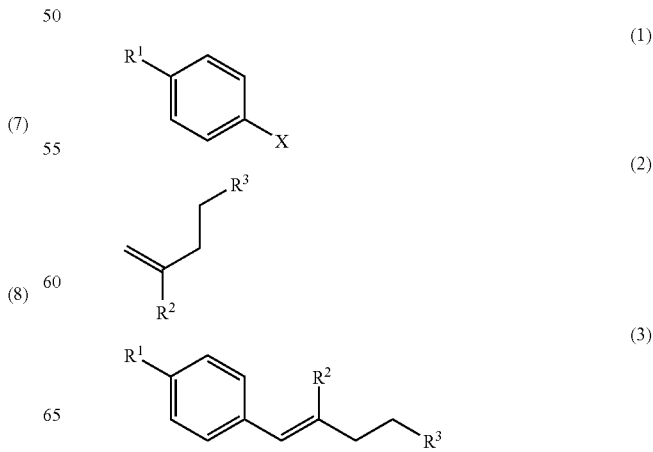

-continued (4)
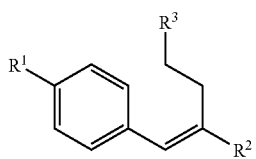

(5)
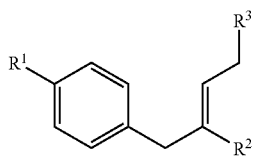

(6)
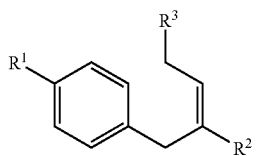

(7)
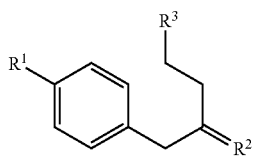

-continued (9)
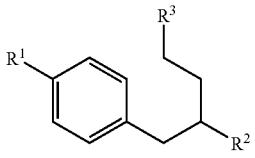

wherein $R^1$ and $R^2$ are independently $C_{1-10}$ alkyl; $R^3$ is halogen or O—Y, wherein Y is selected from the group consisting of hydrogen, alkyl, arylmethyl, alkylsilyl, alkoxycarbonyl, acyl, arylsulfonyl, alkylsulfonyl and dialkylphosphonyl; X is halogen or O—Z, wherein Z is selected from the group consisting of alkyl, arylmethyl, alkylsilyl, alkoxycarbonyl, acyl, arylsulfonyl, alkylsulfonyl and dialkylphosphonyl.

In the present invention, "alkyl group" can be a straight chained or branched alkyl group and preferably, straight chained and branched $C_1$~$C_{10}$ alkyl group and more preferably, straight chained or branched $C_1$~$C_4$ alkyl group.

Hereinafter, the process of the present invention will be described more clearly steps as follows.

In the first step of alkylation, the aromatic compounds having the structure of formula (1) and the alkene compounds having the structure of formula (2) are adopted as the starting materials to produce reaction products which comprises the compounds having the structure of formula (3)~formula (8), as illustrated in reaction formula I.

<Reaction Formula I>

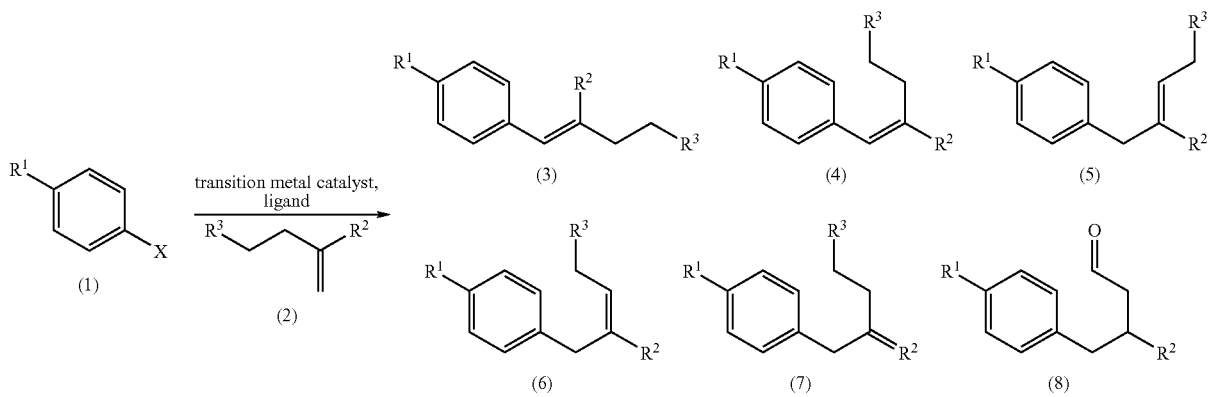

Herein, $R^1$, $R^2$, $R^3$ and X are defined as described above.

Preferably, X is a chlorine or a bromine. In the step i) for the alkylation, solvent can be one or more substances selected from the group comprising acetonitrile, dimethylformamide, acetic acid, dimethylsulfoxide, dimethylacetamide, methanol, ethanol, benzene, toluene, xylene, or tetrahydrofurane.

According to reaction formula I, the aromatic compounds of formula (1), and the alkene compounds of formula (2) are stirred in the presence of transition metal catalysts and phosphine or arsenic compounds to prepare reaction products which comprises the compounds of formula (3) to formula (8) inclusive. If necessary, the mixture of intermediates having structure of formula (3) to formula (7) inclusive and the -continued (8)
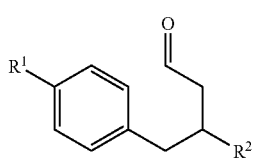

intermediates having structure of formula (8) can be separated by column chromatography or fractional distillation.

In this reaction, the active components of catalysts are the transition metals which are coordinated with the ligands and composed of one or more substances selected from the group comprising Pd, Pt, Ni, Rh, Ir, Ru, Fe and Co. Preferably, the transition metals used as the catalysts can be one or more substances selected from the group comprising Pd, Pt or Ni.

Preferably, the amounts of the catalysts and the ligands used in the step i) can be in the range of 0.01~100 equivalent % respectively. The reaction is not performed completely or the reaction rate become very slow under 0.01 equivalent %, and on the other hand, the reaction is not accomplished economically and may contaminate the environment over 100 equivalent %.

More preferably, the amounts of the catalysts can be in the range of 0.1~20 equivalent % respectively and most preferably, the amount of ligands can be double or more than the amount of transition metal catalyst.

The reaction can be proceeded for 48 hours or less and preferably, until the starting materials disappear completely. At this moment, the reaction is preferable to be maintained at the temperature range of 0° C.~200° C. It is important to adjust the temperature, since at a higher temperature the reaction is proceeded vigorously to generate a large amount of by-products and at a lower temperature, the reaction is rarely proceeded.

More preferably, the temperature can be adjusted at the range of 80° C.~150° C. The reaction can be performed at ambient pressure or at the range of 10~20 atmospheric pressure. It is clearly understood to those skilled in this art that the reaction temperature and the reaction time can be properly controlled depending on the pressures.

The synthetic yield of the reaction can be calculated as follows.

Synthetic yield (%)=(moles of product/moles of reactant)×100     <Equation I>

Practical and preferred embodiments of the present invention will be illustrated in more detail in the following Examples. The present invention is not limited to them and can allow various modifications and alterations performed by those skilled in the art.

EXAMPLE 1-1

Preparation of alkylated products from the mixture of 4-bromotoluene and 3-methyl-3-buten-1-ol To a solution of 14.6 mmol (2.50 g) of 4-bromotolene in 100 mL of acetonitrile, was added 0.73 mmol (164 mg) of palladium acetate, 1.46 mmol (445 mg) of tri-ortho-tolylphosphine, 43.8 mmol (6.1 mL) of triethylamine and 14.6 mmol (1.47 mL) of 3-methyl-3-buten-1-ol. The mixture was refluxed at 80~81° C. under ambient pressure for 24 hours. As illustrated in reaction formula II, the products were separated to the aldehyde and the mixture of the alkenes with column chromatography eluted with hexane and ethyl acetate (hexane:ethyl acetate=4:1). The yield is demonstrated in Table 1.

EXAMPLE 1-2

Preparation of alkylated product from the mixture of 1-bromo-4-ethylbenzene and 3-methyl-3-buten-1-ol To a solution of 1.46 mmol (270 mg) of 4-bromoethylbenzene in 12 mL of acetonitrile, was added 0.073 mmol (16.4 mg) of palladium diacetate, 0.146 mmol (44.5 mg) of tri-ortho-tolylphosphine, 4.38 mmol (0.61 mL) of triethylamine and 1.46 mmol (0.147 mL) of 3-methyl-3-buten-1-ol. The mixture was refluxed at 80~81° C. under ambient pressure for 24 hours. As illustrated in reaction formula II, the products were separated to the aldehyde and the mixture of the alkenes with column chromatography eluted with hexane and ethyl acetate (hexane:ethyl acetate=4:1). The yield is demonstrated in Table 1.

EXAMPLE 1-3

Preparation of alkylated product from the mixture of 1-bromo-4-butylbenzene and 3-methyl-3-buten-1-ol To a solution of 1.46 mmol (311 mg) of 4-bromobutylbenzene in 12 mL of acetonitrile, was added 0.073 mmol (16.4 mg) of palladium diacetate, 0.146 mmol (44.5 mg) of tri-ortho-tolylphosphine, 4.38 mmol (0.61 mL) of triethylamine and 1.46 mmol (0.147 mL) of 3-methyl-3-buten-1-ol. The mixture was refluxed at 80~81° C. under ambient pressure for 24 hours. As illustrated in reaction formula II, the products were separated to the aldehyde and the mixture of the alkenes with column chromatography eluted with hexane and ethyl acetate (hexane:ethyl acetate=4:1). The yield is demonstrated in Table 1.

EXAMPLE 1-4

Preparation of alkylated product from the mixture of trifluoromethanesulfonic acid para-tolyl ester and 3-methyl-3-buten-1-ol To a solution of 1.46 mmol (350 mg) of trifluoromethanesulfonic acid para-tolyl ester in 12 mL of acetonitrile, was added 0.073 mmol (16.4 mg) of palladium diacetate, 0.146 mmol (44.5 mg) of tri-ortho-tolylphosphine, 4.38 mmol (0.61 mL) of triethylamine and 1.46 mmol (0.147 mL) of 3-methyl-3-buten-1-ol. The mixture was refluxed at 80~81° C. under ambient pressure for 24 hours. As illustrated in reaction formula II, the products were separated to the aldehyde and the mixture of the alkenes with column chromatography eluted with hexane and ethyl acetate (hexane:ethyl acetate=4:1). The yield is demonstrated in Table 1.

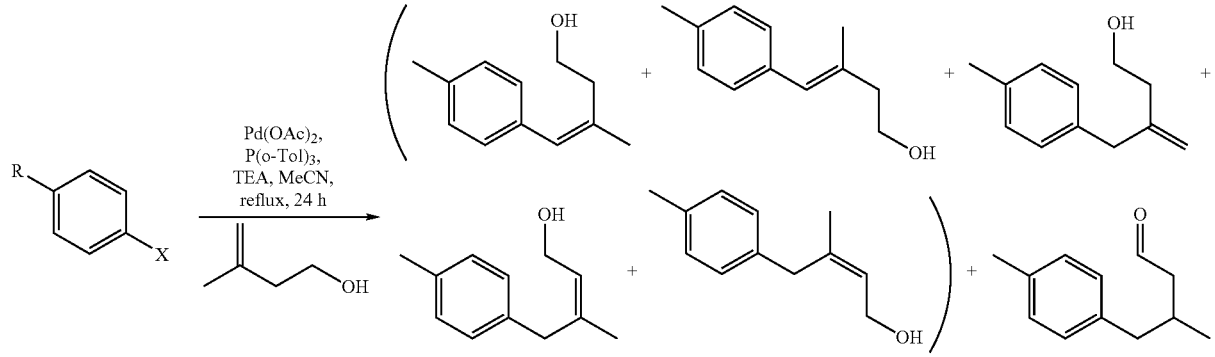

<Reaction Formula II>

TABLE 1

| Items | Exam. 1-1 | Exam. 1-2 | Exam. 1-3 | Exam. 1-4 |
|---|---|---|---|---|
| R | methyl | ethyl | butyl | methyl |
| X | Br | Br | Br | OTf |
| reactant (mmol) | 14.6 | 1.46 | 1.46 | 1.46 |
| alkenes (mmol) | 8.67 | 0.80 | 0.77 | 0.58 |
| aldehyde (mmol) | 5.88 | 0.59 | 0.55 | 0.45 |
| Yield of alkenes (%) | 59 | 55 | 53 | 40 |
| Yield of aldehyde (%) | 40 | 40 | 38 | 31 |

Next, the second step of the present invention will be described more specifically.

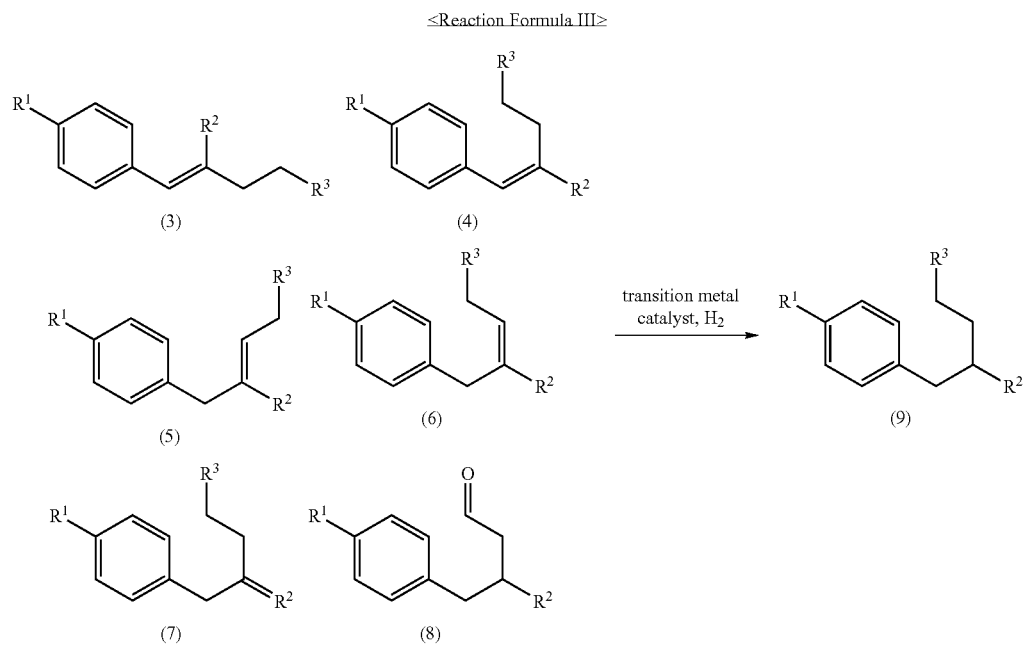

≤Reaction Formula III≥

For the reduction, the double bonds in the reaction products of formula (3) to formula (8) inclusive prepared in step i), are reduced selectively in the presence of the transition metal catalysts to prepare the compound having the structure of formula (9), while the double bonds in the aromatic region of the reaction products of formula (3) to formula (8) inclusive are not reduced.

The transition metal catalysts can be one or more substances selected from the group comprising Pd, Pt, Ni, Rh, Ir, Ru, Fe or Co, preferably, can be one or more substances selected from Pd, Pt and Ni. More preferably, the catalyst can be transition metals dispersed on inert supports, and most preferably, Pt or Pd carried on active carbon.

Preferably, the amount of the transition metal catalysts can be in the range of 0.01~100 equivalent % and more preferably, in the range of 0.05~20 equivalent %, as described in the step i). Preferably, the reaction can be proceeded for 48 hours or less and more preferably, until the starting materials disappear completely.

At this moment, hydrogen gas can be injected directly or transferred through hydrogen-transfer reagents. The reaction can be performed under 1~50 atmospheric pressure. It is clearly understood to those skilled in this art that the reaction temperature and the reaction time can be properly controlled depending on the pressures.

EXAMPLE 2-1

Preparation of 3-methyl-4-para-tolyl-1-butanol from the reaction products prepared in Example 1

To a solution of 7.6 mmol (1.34 g) of the product of Example 1 in 50 mL of ethyl acetate, was added 0.38 mmol (808.6 mg) of palladium carried on active carbon in 5-weight %. And then the reaction mixture was stirred while running hydrogen gas at 20 cc/min of flow velocity at room temperature under ambient pressure for 12~24 hours. Afterward, the crude product was filtered, and then the filtrate was concentrated and purified with column chromatography or fractional distillation so as to prepare the pure product. At this moment, palladium carried on active carbon can be separated and recycled in a solid powder.

As illustrated in reaction formula IV, the mixture of the alkenes was converted to the same product entirely. The amount of product, the amount of catalyst and the synthetic yield are demonstrated in Table 2.

<Reaction Formula IV>

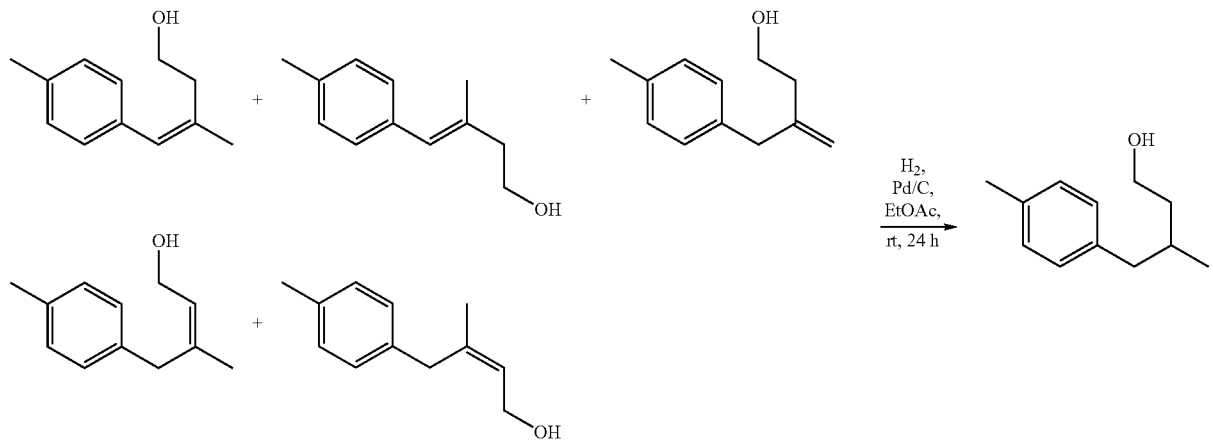

| Items | Exam. 2-1-1 | Exam. 2-1-2 | Exam. 2-1-3 | Exam. 2-1-4 |
|---|---|---|---|---|
| reactant (mmol) | 6.20 | 7.35 | 6.45 | 8.61 |
| Product (mmol) | 5.33 | 6.25 | 5.61 | 7.92 |
| Amount of catalyst (mmol) | 0.62 | 0.37 | 0.64 | 0.43 |
| reaction time (hour) | 12 | 12 | 24 | 24 |
| yield (%) | 86 | 85 | 87 | 92 |

TABLE 2

EXAMPLE 2-2

Preparation of 3-methyl-4-para-tolyl-1-butanol from the reaction products prepared in Example, by using hydrogen gas in the presence of palladium carried on active carbon To a solution of 8.67 mmol (1.52 g) of the mixture of the alkenes and 5.88 mmol (1.03 g) of the aldehydes obtained from preparation example 1 in 100 mL of ethyl acetate, was added 0.73 mmol (2.84 g) of platinium carried on active carbon in a high pressure reactor. And then the reaction mixture was stirred under 20 atmospheric pressure at room temperature for 24 hours. Afterward, the crude product was filtered, and then the filtrate was concentrated and purified with column chromatography or fractional distillation.

Consequently, one kind of reduced product, 3-methyl-4-para-tolyl-1-butanol was prepared to attain 90% of yield as illustrated in reaction formula V. At this moment, platinium carried on active carbon can be separated and recycled in a solid powder.

<Reaction Formula V>

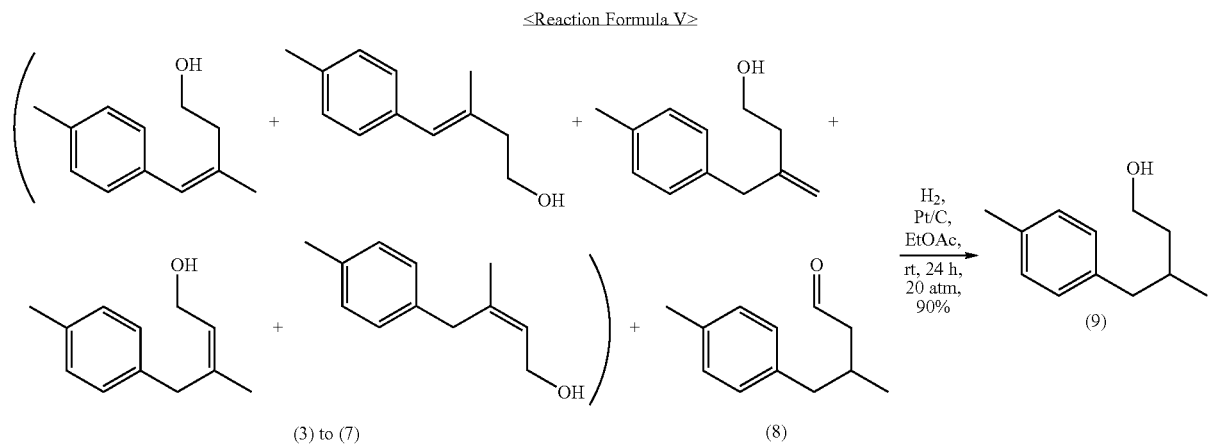

The cyclization reaction, the third step of present invention, will be illustrated more specifically.

For the cyclization, the second intermediate of formula (9) manufactured above is subject to cyclize in the presence of catalyst to furnish 2,6-dialkyltetralin having the structure of formula (10). The reaction can be proceeded at the temperature range of 50~300° C. It is important to adjust the reaction temperature, since at a higher temperature, the reaction is proceeded vigorously to generate a large amount of by-products and at a lower temperature, the reaction is rarely proceeded. More preferably, the reaction is adjusted at the temperature range of 100° C.~200° C. It is advantageous that the reaction is performed with a microwave reactor to reduce the reaction time and the temperature.

Preferably, the catalyst used for the cyclization can be selected among Lewis acid series, inorganic acid series, acidic resin series, acidic zeolite series and the like. The Lewis acid catalyst can be one or more substances selected from the group comprising iron halide ($FeX_n$), titanium halide ($TiX_n$), titanium alkoxide ($Ti(OR)_4$), titanium oxide ($TiO_2$), aluminum halide ($AlX_3$), aluminum alkoxide ($Al(OR)_3$), tin halide ($SnX_n$), boron trihalide ($BX_3$), magnesium halide ($MgX_2$), zinc halide ($ZnX_2$), and the like.

Besides, the inorganic acid catalyst can be one or more substances selected from a group comprising hydrochloric acid, sulfuric acid, nitric acid, hydrofluoric acid, phosphoric acid, hydriodic acid and the like. In addition, the acidic resin catalyst can be one or more substances selected from the group comprising Amberlyst, Amberlite, Dowex, Zipax, Nafion, and the like.

Preferably, the amounts of the catalyst can be in the range of 0.01~1,000 equivalent %. The reaction is not performed completely or the reaction rate become slow under 0.01 equivalent % and the reaction is not accomplished economically and may contaminate the environment over 1,000 equivalent %. More preferably, the amount of catalyst can be in the range of 0.1~500 equivalent %.

Preferably, at the cyclization step, the solvent can be one or more substances that are selected from the group comprising hydrocarbons, halogenated hydrocarbons, hetero atom-containing hydrocarbons, and the like. More preferably, the solvent can be one or more substances selected from the group comprising toluene, xylene, chlorobenzene, bromobenzene, chlorotoluene, bromotoluene, dioxane, 1,1,2-trichloroethane, trichloroethylene, 1,2-dichloroethane, and the like.

Preferably, the reaction can be proceeded for in the range of 10 minutes~48 hours and more preferably, until the starting materials disappear completely. Both Iron halide ($FeX_n$) and Nafion resin can partially convert the starting materials to 2,6-dialkylnaphthalene without an extra-catalyst for the dehydrogenation as illustrated in following Examples 3-1 and 3-4.

2,6-Dialkyltetralin prepared in the cyclization reaction of the present invention is converted to 2,6-dialkylnaphthalene by dehydrogenation under various catalysts. The dehydrogenation and proper catalysts have been disclosed in U.S. Pat. No. 5,118,892, U.S. Pat. No. 5,189,234, U.S. Pat. No. 3,775, 498 and U.S. Pat. No. 3,781,375. This reaction may be accomplished under gas or liquid phase preferably, 2,6-DMT can be dehydrogenated in gas phase by using proper catalysts, for example, composed of alumina, about 0.05~5.0 weight % of platinium or palladium, about 0.14 weight % or less of halides at about 600° F.~900° F. under 0.01~25 atmospheric pressure and at 0.1~20/h of weight hourly space velocity.

EXAMPLE 3-1

Preparation of 2,6-DMN and 2,6-DMT through cyclization of 3-methyl-4-para-tolyl-1-butanol manufactured in Example 2 in the presence of iron (III) chloride ($FeCl_3$) catalyst 1.12 mmol (182 mg) of iron (III) chloride was transferred into a pressure tube in a glovebox, and then a solution of 3-methyl-4-para-tolyl-1-butanol (100 mg, 0.56 mmol) in chlorobenzene (5.6 mL), was added into the pressure tube. The mixture was stirred at 200° C. for 2 hours. Afterward, the crude product was filtered, and then the filtrate was concentrated and purified with column chromatography or fractional distillation to obtain the end product. The products of this Example were analyzed by $^1H$ NMR, $^{13}C$ NMR, mass spectroscopy and gas chromatography.

Consequently, it is confirmed to be the mixture of 2,6-DMN and 2,6-DMT as illustrated in reaction formula VI. The amount of reactant, the composition of products, the synthetic yield and the amount of catalyst is demonstrated in Table 3.

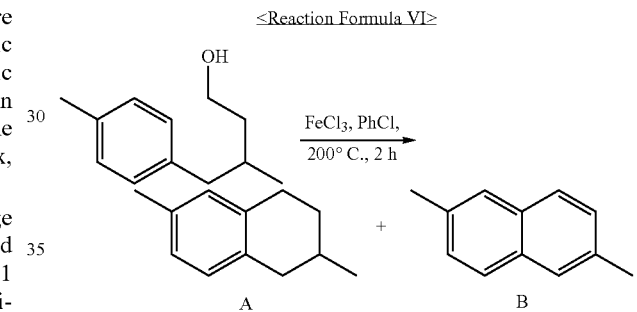

<Reaction Formula VI>

TABLE 3

| Items | Exam. 3-1-1 | Exam. 3-1-2 | Exam. 3-1-3 | Exam. 3-1-4 |
|---|---|---|---|---|
| catalyst of cyclization | $FeCl_3$ | $FeCl_3$ | $FeCl_3$ | $FeCl_3$ |
| reactant (mmol) | 0.28 | 0.28 | 0.28 | 0.28 |
| amount of catalyst (mmol) | 0.28 | 0.56 | 1.12 | 2.80 |
| product A (mmol) | 0.213 | 0.196 | 0.197 | 0.126 |
| product B (mmol) | 0.014 | 0.023 | 0.039 | 0.070 |
| yield A + B (%) | 81 | 78 | 84 | 70 |

EXAMPLE 3-2

Preparation of 2,6-DMT through cyclization of 3-methyl-4-para-tolyl-1-butanol manufactured in Example 2 in the presence of titanium tetrachloride ($TiCl_4$) catalyst To a solution of 3-methyl-4-para-tolyl-1-butanol (50 mg, 0.28 mmol) manufactured in Example 2 in chlorobenzene (2.8 mL) in pressure tube, was added 0.56 mL (0.56 mmol) of 1 M solution of titanium tetrachloride in methylene chloride ($CH_2Cl_2$) under nitrogen and reacted at 200° C. for 2 hours. Afterward, the crude product was filtered, and then the filtrate was concentrated and purified with column chromatography or fractional distillation to obtain the end product.

The products of this Example were analyzed by $^1$H NMR (See FIG. 1), $^{13}$C NMR, mass spectroscopy and gas chromatography. Consequently, pure 2,6-DMT can be obtained as illustrated in the reaction formula VII. The amount of reactant, the synthetic yield and the amount of catalyst are demonstrated in Table 4.

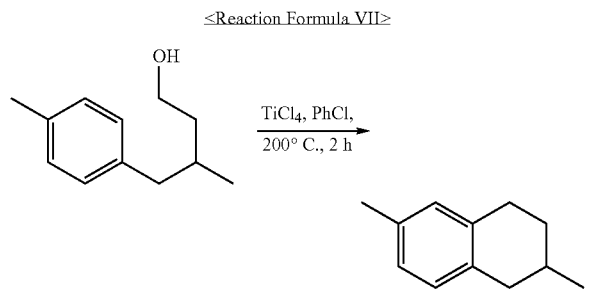

<Reaction Formula VII>

TABLE 4

| Items | Exp. 3-1-1 | Exp. 3-1-2 | Exp. 3-1-3 | Exp. 3-1-4 |
|---|---|---|---|---|
| catalyst of cyclization | TiCl$_4$ | TiCl$_4$ | TiCl$_4$ | TiCl$_4$ |
| reactant (mmol) | 0.28 | 0.28 | 0.28 | 0.28 |
| amount of catalyst (mmol) | 0.28 | 0.56 | 1.12 | 2.24 |
| product (mmol) | 0.224 | 0.235 | 0.218 | 0.210 |
| yield (%) | 80 | 84 | 78 | 75 |

EXAMPLE 3-3

Preparation of 2,6-DMT through cyclization of 3-methyl-4-para-tolyl-1-butanol manufactured in Example 2 in the presence of Amberlyst 15 catalyst (1) Washing of Amberlyst 15

Amberlyst 15 is a resin containing 4.7 mmol of H$^+$ ion per 1 g. Before use, it should be washed with methanol, 2 N of hydrochloric acid and distilled water in regular order. Afterward, the resin was rinsed by using acetone and dried at room temperature to enhance the catalyst activity.

(2) To a solution of 3-methyl-4-para-tolyl-1-butanol (50 mg, 0.28 mmol) manufactured in Example 2 in chlorobenezene (2.8 mL) in pressure tube, was added 2.8 mmol (593 mg) of Amberlyst 15 under nitrogen and reacted at 200° C. for 2 hours. Afterward, the reaction mixture was filtered to recover the Amberlyst 15 and the recovered resin was washed with methylene chloride (10 mL×3). The filtrate and the washings were concentrated and purified with column chromatography or fractional distillation to obtain the end product.

The product of Example 3-3 was analyzed by $^1$H NMR (See FIG. 1), $^{13}$C NMR, mass spectroscopy and gas chromatography. Consequently, pure 2,6-DMT can be obtained. The amount of reactant, the synthetic yield and the amount of catalyst are demonstrated in Table 5. Also, Amberlyst 15 can be re-used several times without an extra-washing step as illustrated in Table 5.

EXAMPLE 3-4

Preparation of 2,6-DMT and 2,6-DMN through cyclization of 3-methyl-4-para-tolyl-1-butanol manufactured in Example 2 in the presence of Nafion catalyst To a solution of 3-methyl-4-para-tolyl-1-butanol (50 mg, 0.28 mmol) manufactured in Example 2 in chlorobenezene (2.8 mL) in pressure tube, was added 950 mg of Nafion, which is a strongly acidic ion exchange resin, under nitrogen and reacted at 200° C. for 2 hours. Afterward, the reaction mixture was filtered to recover the Nafion and the recovered resin was washed with methylene chloride (10 mL×3). The filtrate and the washings were concentrated and purified with column chromatography or fractional distillation to obtain the end product.

The products of this Example was analyzed by $^1$H NMR (See FIG. 1), $^{13}$C NMR, mass spectroscopy and gas chromatography. Consequently, the mixture of 2,6-DMT and 2,6-DMN can be obtained as illustrated in reaction formula VIII. The amount of reactant, the composition of products, the synthetic yield and the amount of catalyst is demonstrated in Table 5. Also, Nafion can be re-used several times without an extra-washing step as illustrated in Table 5.

<Reaction Formula VIII>

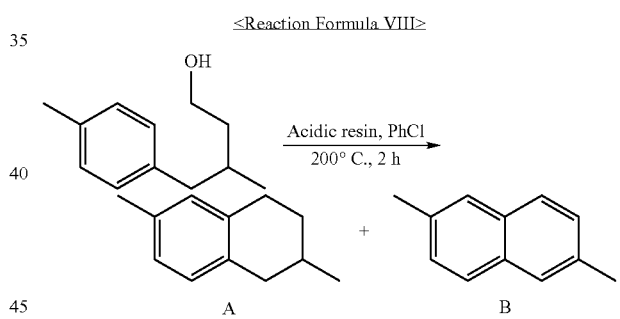

A  B

EXAMPLE 3-5

Preparation of 2,6-DMT through cyclization of 3-methyl-4-para-tolyl-1-butanol manufactured in Example 2 in the presence of zeolite H—Y To a solution of 3-methyl-4-para-tolyl-1-butanol (50 mg, 0.28 mmol) manufactured in Example 2 in chlorobenezene (2.8 mL) in pressure tube, was added 0.5 g of zeolite under nitrogen and reacted at 200° C. for 2 hours. Afterward, the reaction mixture was filtered, the filtrate was concentrated and purified with column chromatography or fractional distillation to obtain the end product.

The product of the present invention was analyzed by $^1$H NMR (See FIG. 1), $^{13}$C NMR, mass spectroscopy and gas chromatography. Consequently, pure 2,6-DMT can be obtained. The amount of reactant, the synthetic yield and the amount of catalyst are demonstrated in Table 5.

TABLE 5

| Items | catalyst of cyclization | reactant (mmol) | product A (mmol) | product B (mmol) | yield A + B (%) |
|---|---|---|---|---|---|
| Exp. 3-3-1 | Amberlyst 15[a] | 0.28 | 0.232 | — | 83 |
| Exp. 3-3-2 | | 0.28 | 0.238 | — | 85 |
| Exp. 3-3-3 | | 0.28 | 0.230 | — | 82 |
| Exp. 3-4-1 | Nafion[b] | 0.28 | 0.123 | 0.092 | 77 |
| Exp. 3-4-2 | | 0.28 | 0.123 | 0.070 | 69 |
| Exp. 3-4-3 | | 0.28 | 0.120 | 0.053 | 62 |
| Exp. 3-5-1 | Zeolite H-Y | 0.28 | 0.210 | — | 75 |

[a] Amberlyst 15 used in experiment 1 is recycled in experiment 2 and 3.
[b] Nafion used in experiment 4 is recycled in experiment 5 and 6.

EXAMPLE 3-6

Preparation of 2,6-DMT through cyclization of 3-methyl-4-para-tolyl-1-butanol manufactured in Example 2 in the presence of a selected catalyst in a micro wave reactor To a solution of 3-methyl-4-para-tolyl-1-butanol (50 mg, 0.28 mmol) manufactured in Example 2 in chlorobenezene (2.8 mL) in pressure tube, was added 0.56 mL (0.56 mmol) of 1 M solution of titanium tetrachloride in methylene chloride ($CH_2Cl_2$) and reacted at 100° C. for 10 minutes in micro wave reactor. Afterward, the crude product was filtered, and then the filtrate was concentrated and purified with column chromatography or fractional distillation to obtain the end product.

The products of this Example were analyzed by $^1$H NMR (See FIG. 1), $^{13}$C NMR, mass spectroscopy and gas chromatography. Consequently, pure 2,6-DMT can be obtained as illustrated in reaction formula IX. The amount of reactant, the synthetic yield and the amount of catalyst are demonstrated in Table 6.

<Reaction Formula IX>

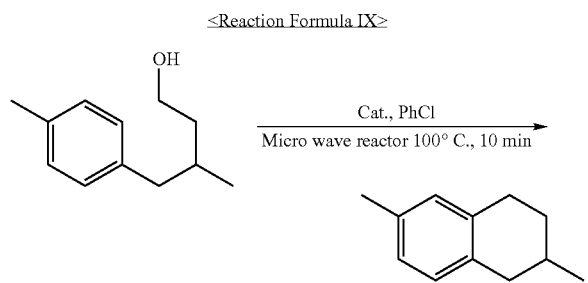

TABLE 6

| Items | Exam. 3-6-1 | Exam. 3-6-2 |
|---|---|---|
| catalyst of cyclization | $TiCl_4$ | Amberlyst 15 |
| reactant (mmol) | 0.28 | 0.28 |

TABLE 6-continued

| Items | Exam. 3-6-1 | Exam. 3-6-2 |
|---|---|---|
| Amount of catalyst (mmol) | 0.56 | 2.80 |
| product (mmol) | 0.241 | 0.235 |
| yield (%) | 86 | 84 |

EXAMPLE 4

Preparation of 2,6-DMT from mixture of 4-bromotoluene and 3-methyl-3-buten-1-ol through alkylation, reduction and cyclization To a solution of 14.6 mmol (2.50 g) of 4-bromotolene in 100 mL of acetonitrile, was added 0.73 mmol (164 mg) of palladium acetate, 1.46 mmol (445 mg) of tri-ortho-tolylphosphine, 43.8 mmol (6.1 mL) of triethylamine and 14.6 mmol (1.47 mL) of 3-methyl-3-buten-1-ol.

The mixture was refluxed at 80~81° C. under ambient pressure for 24 hours. As illustrated in reaction formula X, the products were separated to the aldehyde and the mixture of the alkenes with column chromatography eluted with hexane and ethyl acetate (hexane:ethyl acetate=4:1).

Consequently, the aldehyde compound was obtained in 40% yield and mixture of alkene compounds were obtained in 59% yield.

To a solution of 8.67 mmol (1.52 g) of the mixture of the alkenes and 5.88 mmol (1.03 g) of the aldehydes obtained from alkylation step in 100 mL of ethyl acetate, was added 0.73 mmol (2.84 g) of platinium carried on active carbon in a high pressure reactor.

And then the reaction mixture was stirred under 20 atmospheric pressure at room temperature for 24 hours. Afterward, the crude product was filtered, and then the filtrate was concentrated and purified with column chromatography or fractional distillation. Consequently, one kind of reduced product, 3-methyl-4-para-tolyl-1-butanol was obtained 90% of yield as illustrated in reaction formula X. At this moment, platinium carried on active carbon can be separated and recycled in a solid powder.

To a solution of 3-methyl-4-para-tolyl-1-butanol (50 mg, 0.28 mmol) manufactured from reduction step in chlorobenezene (2.8 mL) in pressure tube, was added 2.8 mmol (593 mg) of Amberlyst 15 under nitrogen and reacted at 200° C. for 2 hours. Afterward, the reaction mixture was filtered to recover the Amberlyst 15 and the recovered resin was washed with methylene chloride (10 mL×3). The filtrate and the washings were concentrated and purified with column chromatography or fractional distillation to obtain the end product.

Consequently, pure 2,6-DMT was obtained in 84% yield and it was analyzed by $^1$H NMR (See FIG. 1), $^{13}$C NMR, mass spectroscopy and gas chromatography.

<Reaction Formula X>

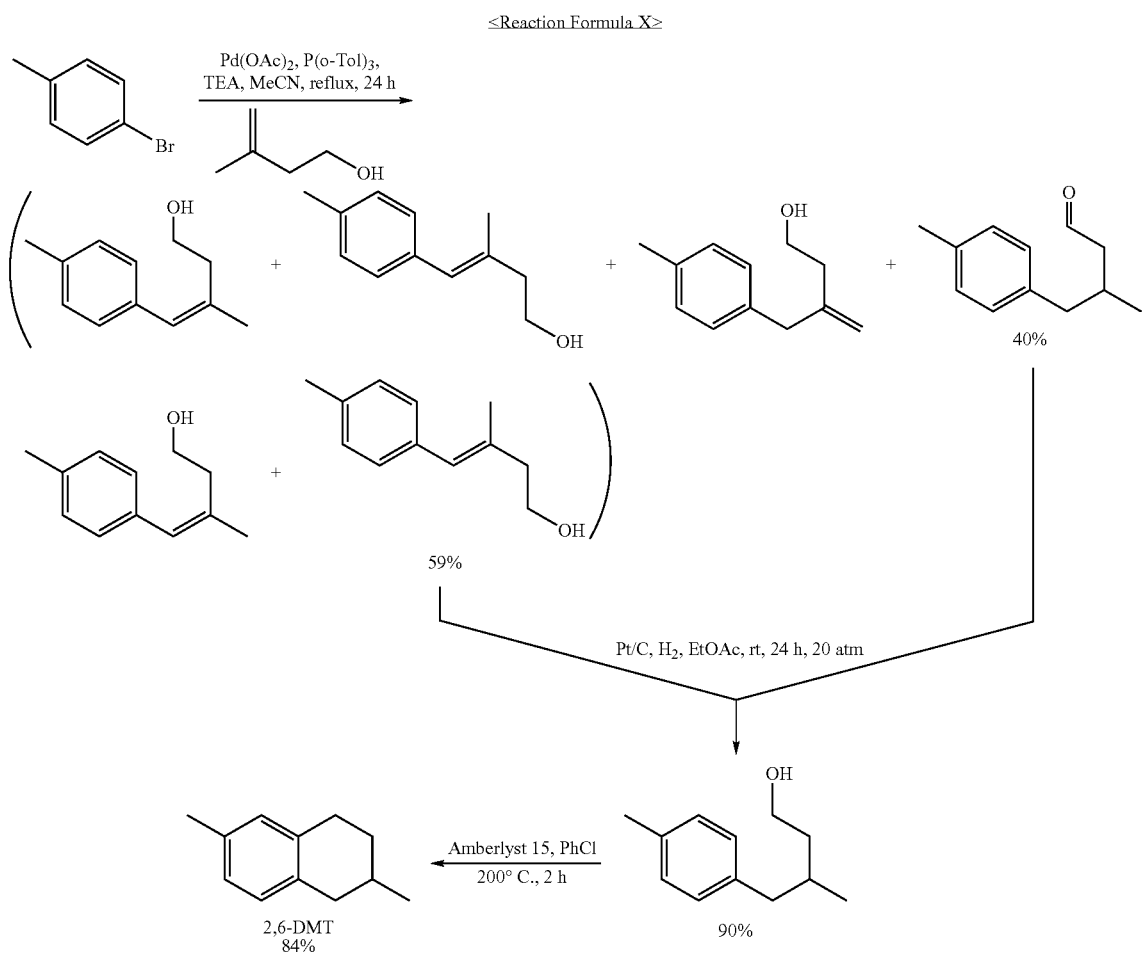

Those skilled in the art will appreciate that the conceptions and specific embodiments disclosed in the foregoing description and Examples may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

INDUSTRIAL APPLICABILITY

As illustrated and confirmed above, the present invention provides a novel process for highly selective preparation 2,6-dialkyltetralin to exclude additional steps of separation and isomerization. Therefore, it is advantageous to improve the synthetic yield of the end product, 2,6-DMT, to simplify the operation and thus to reduce the production cost.

What is claimed is:

1. A process for the preparation of a compound of formula (9), which comprises:
    i) a step for alkylating an aromatic compound of formula (1) with an alkene compound of formula (2) in the presence of catalyst to produce the reaction products which comprises the compounds of formulas (3) to (8); and
    ii) a step for reducing the reaction products obtained in the above step i) to produce the compound of formula (9),

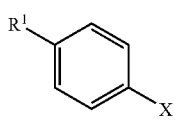 (1)

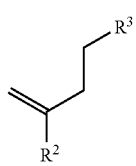 (2)

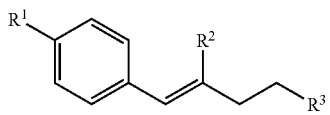 (3)

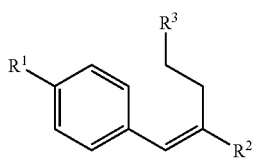 (4)

-continued

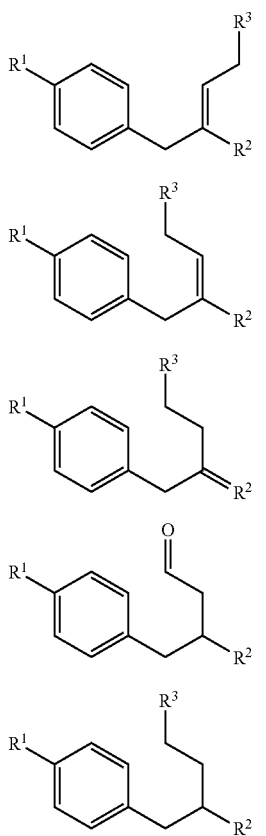

wherein, $R^1$ and $R^2$ are independently $C_{1\text{-}10}$ alkyl; $R^3$ is halogen or O—Y wherein Y is selected from the group consisting of hydrogen, alkyl, arylmethyl, alkylsilyl, alkoxycarbonyl, acyl, arylsulfonyl, alkylsulfonyl and dialkylphosphonyl; and X is halogen or O—Z wherein Z is selected from the group consisting of alkyl, arylmethyl, alkylsilyl, alkoxycarbonyl, acyl, arylsulfonyl, alkylsulfonyl and dialkylphosphonyl.

2. The process for the preparation of the compound of formula (9) according to claim 1, wherein X is chloride, bromide or iodide.

3. The process for the preparation of compound (9) according to claim 1, in which the step i) proceeds in the solvents selected from the group consisting of acetonitrile, N,N-dimethylformamide, N,N-dimethylacetamide, 1-methyl-2-pyrolidinone, dimethylsulfoxide, methanol, ethanol, benzene, toluene, xylene, tetrahydrofuran and a mixture thereof.

4. The process for the preparation of compound (9) according to claim 1, wherein the catalyst of the step i) is transition metal selected from the group consisting of Pd, Pt, Ni, Rh, Ir, Ru, Fe, Co and their organometallic compounds with one or more ligands.

5. The process for the preparation of the compound of formula (9) according to claim 4, wherein said catalyst contains phosphine or arsenic compounds.

6. The process for the preparation of the compound of the formula (9) according to claim 4, in which the amount of said catalyst is in the range of 0.01~100 equivalent %.

7. The process for the preparation of the compound of formula (9) according to claim 6, in which the amount of the catalyst is in the range of 0.05~20 equivalent %.

8. The process for the preparation of the formula (9) according to claim 1, the step i) is performed at the temperature range of 0° C.~200° C.

9. The process for the preparation of the compound of formula (9) according to claim 4, said the catalyst is carried on inert supports or on active carbon.

10. The process for the preparation of the compound of formula (9) according to claim 1, wherein the step ii) is performed under 1~50 atmospheric pressure.

11. A process for the preparation of 2,6-dialkyltetralin of formula (10), which comprises:

i) a step for alkylating an aromatic compound of formula (1) with an alkene compound of formula (2) in the presence of catalyst to produce the reaction products which comprises the compounds of formula (3) to (8);

ii) a step for reducing the reaction products obtained in the above step i) to produce the compound of formula (9), and iii) a step for cyclizing the compound of formula (9) obtained in the above step ii) to produce the compound of formula (10):

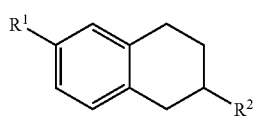

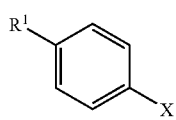

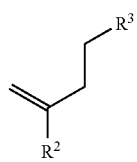

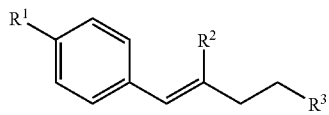

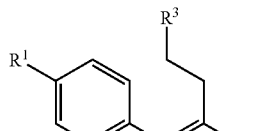

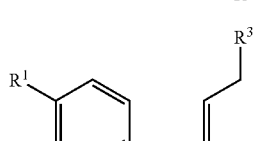

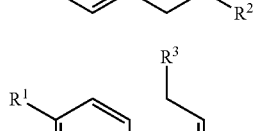

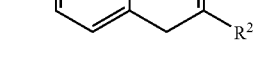

-continued

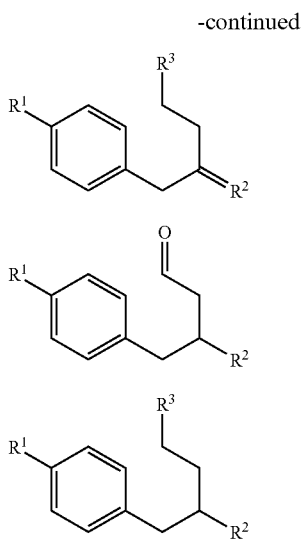

(7)

(8)

(9)

wherein $R^1$ and $R^2$ are independently $C_{1-10}$ alkyl; $R^3$ is halogen or O—Y, wherein Y is selected from the group consisting of hydrogen, alkyl, arylmethyl, alkylsilyl, alkoxycarbonyl, acyl, arylsulfonyl, alkylsulfonyl and dialkylphosphonyl; and X is halogen or O—Z wherein Z is selected from the group consisting of alkyl, arylmethyl, alkylsilyl, alkoxycarbonyl, acyl, arylsulfonyl, alkylsulfonyl and dialkylphosphonyl.

12. The process for preparing 2,6-dialkyltetralin according to claim 11, in which the compound of formula(9) is cyclized in the presence of one or more catalyst selected from the group consisting of Lewis acid catalyst, inorganic acid catalyst, acidic resin catalyst and acidic zeolite catalyst.

13. The process for preparing 2,6-dialkyltetralin according to claim 12, in which the Lewis acid catalyst is composed of one or more substances selected from the group consisting of iron halide ($FeX_n$), titanium halide ($TiX_n$), titanium alkoxide ($Ti(OR)_4$), titanium oxide ($TiO_2$), aluminum halide ($AlX_3$), aluminum alkoxide ($Al(OR)_3$), tin halide ($SnX_n$), borone trihalide ($BX_3$), magnesium halide ($MgX_2$) and zinc halide ($ZnX_2$).

14. The process for preparing 2,6-dialkyltetralin according to claim 12, in which said inorganic acid catalyst is composed of one or more substances selected from the group consisting of hydrochloric acid, sulfuric acid, nitric acid, hydrofluoric acid, phosphoric acid and hydriodic acid.

15. The process for preparing 2,6-dialkyltetralin according to claim 12, in which the amount of the catalyst is in the range of 0.01~1000 equivalent %.

16. The process for preparing 2,6-dialkyltetralin according to claim 11, in which the cyclization is performed at the range of 50~300° C. in the step (c).

17. The process for preparing 2,6-dialkyltetralin according to claim 11, in which the cyclization reaction is performed under the conditions of using one or more apparatus selected from the group consisting of high-pressure reactor, a pressure tube and a microwave reactor.

18. The process for preparing 2,6-dialkyltetralin according to claim 11, in which the cyclization is performed in the solvents selected from the group consisting of hydrocarbon, halogenized hydrocarbon and heteroatom-containing hydrocarbon and a mixture thereof.

19. The process for preparing 2,6-dialkyltetralin according to claim 18, in which the cyclization is performed in the solvents selected from the group consisting of toluene, xylene, chlorobenzene, bromobenzene, chlorotoluene, bromotoluene, dioxane and a mixture thereof.

* * * * *